United States Patent [19]

Katsushima et al.

[11] 4,084,059
[45] Apr. 11, 1978

[54] 2-HYDROXY-1,1,2,3,3-PENTAHYDRO-PERFLUOROALKYL DERIVATIVES, AND THEIR PRODUCTION AND USE

[75] Inventors: Atsuo Katsushima, Higashiosaka; Iwao Hisamoto, Suita; Shoshin Fukui, Toyonaka; Chiaki Maeda, Settsu; Akitoshi Iwatani, Yao; Takahisa Kato, Settsu; Masayuki Nagai, Settsu; Hiroyuki Shinkai, Settsu; Masayuki Asaoka, Kyoto, all of Japan

[73] Assignee: Daikin Kogyo Co., Ltd., Osaka, Japan

[21] Appl. No.: 538,507

[22] Filed: Jan. 6, 1975

Related U.S. Application Data

[60] Division of Ser. No. 299,741, Oct. 24, 1972, Pat. No. 3,870,748, which is a continuation-in-part of Ser. No. 877,497, Nov. 7, 1969, abandoned.

[30] Foreign Application Priority Data

| Nov. 18, 1968 | Japan | 43-84276 |
|---|---|---|
| Feb. 7, 1969 | Japan | 44-9524 |
| Dec. 5, 1968 | Japan | 43-89252 |
| Dec. 19, 1968 | Japan | 43-93513 |
| Dec. 19, 1968 | Japan | 43-93514 |
| Mar. 10, 1969 | Japan | 44-18411 |
| Sep. 18, 1969 | Japan | 44-74146 |

[51] Int. Cl.² .............. C07C 69/76; C07C 69/34; C07C 69/52
[52] U.S. Cl. .............................................. 560/87
[58] Field of Search .............. 260/484 P; 560/87, 181, 560/182

[56] References Cited

U.S. PATENT DOCUMENTS

| 3,057,890 | 10/1962 | De Groote | 260/484 P |
|---|---|---|---|
| 3,385,904 | 5/1968 | Pavlik | 260/485 F |
| 3,433,824 | 3/1969 | Horsley | 260/469 |
| 3,870,748 | 3/1975 | Katsushima et al. | 260/475 F |

Primary Examiner—Anton H. Sutto
Attorney, Agent, or Firm—Bierman & Bierman

[57] ABSTRACT

A 2-hydroxy-1,1,2,3,3-pentahydroperfluoroalkyl derivative of either one of the formulae:

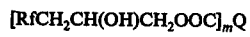

and

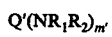

wherein Rf is a perfluoroalkyl, an ω-hydro-perfluoroalkyl or an ω-chloro-perfluoroalkyl group having 4 to 20 carbon atoms, Q is a hydrocarbon residue having a valency corresponding to $m$ which may contain one or more of —O—, —COO— and —OH in and/or on the chain, Q' is a hydrogen atom or a hydrocarbon residue having a valency corresponding to $m'$ which may contain one or more of —O—, —COO—, —NH—, —N= and

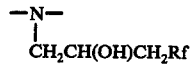

in the chain, $R_1$ and $R_2$ are each a hydrogen atom or a group of the formula: —CH$_2$CH(OH)CH$_2$Rf, at least one of $R_1$ and $R_2$ being —CH$_2$CH(OH)CH$_2$Rf, $m$ is an integer of not less than 2 and $m'$ is an integer of not less than 1, which is useful as an oil-repellent agent or an anti-soiling agent for fibrous materials.

1 Claim, No Drawings

2-HYDROXY-1,1,2,3,3-PENTAHYDRO-PERFLUOROALKYL DERIVATIVES, AND THEIR PRODUCTION AND USE

This is a division of our copending application Ser. No. 299,741, filed Oct. 24, 1972, now U.S. Pat. No. 3,870,748, which is a continuation-in-part application of our copending application Ser. No. 877,497 now abandoned, filed Nov. 17, 1969.

The present invention relates to 2-hydroxy-1,1,2,3,3-pentahydro-perfluoroalkyl derivatives, and their production and use. More particularly, it relates to new and useful 2-hydroxy-1,1,2,3,3-pentahydro-perfluoroalkyl derivatives, to compositions containing same suitable for treating fibrous materials to render them oleophobic and anti-soiling, and to fabrics and fibers which have been sized or coated with the same so as to have been rendered oleophobic and anti-soiling.

The perfluoroalkyl compounds of the present invention can be classified into two groups, i.e.

(1) Carboxylic ester compounds of the formula:

[RfCH$_2$CH(OH)CH$_2$OOC]$_m$Q    [IA]

wherein Rf is a perfluoroalkyl group, an ω-hydro-perfluoroalkyl group or an ω-chloro-perfluoroalkyl group having 4 to 20 carbon atoms, Q is a hydrocarbon residue having a valency corresponding to $m$ which may contain one or more of —O—, —COO— and —OH in and/or on the chain and $m$ is an integer of not less than 2; and (2) Amine compounds of the formula:

Q'(NR$_1$R$_2$)$_{m'}$    [IB]

wherein Q' is a hydrogen atom or a hydrocarbon residue having a valency corresponding to $m'$ which may contain one or more of —O—, —COO—, —NH—, —N= and

in the chain, R$_1$ and R$_2$ are each a hydrogen atom or a group of the formula: —CH$_2$CH(OH)CH$_2$Rf, at least one of R$_1$ and R$_2$ being —CH$_2$CH(OH)CH$_2$Rf, $m'$ is an integer of not less than 1 and Rf is as defined above.

Hitherto, there have been proposed various methods for imparting anti-soiling property to fibrous materials. For instance, fabrics made of hydrophobic synthetic fibers or fabrics processed with a hydrophobic synthetic resin are treated with a solution or suspension of a hydrophilic substance such as polymers having acrylic acid as the unit constituent, polyethylene glycol derivatives and carboxymethyl cellulose. As a result of such treatment, soils attached to the fabrics can be eliminated upon laundering. This method, however, fails to prevent soil attachment itself. Further, for instance, fabrics are treated with a solution or dispersion of polymers of C$_8$F$_{17}$SO$_2$N(C$_2$H$_5$)CH$_2$CH$_2$OOCCH=CH$_2$ or C$_8$H$_{17}$CH$_2$CH$_2$OOCC(CH$_3$)=CH$_2$ or of chromic acid compounds having a polyfluoroalkyl group such as C$_7$F$_{15}$COOCr$_2$(OH)Cl$_4$ to impart oil-repellent property to them whereby the attachment of oily and aqueous stains is prevented. However, it is quite difficult to remove the once attached stain by laundering, and stained parts increase during laundering by adsorption and preservation of soils contained in washings on the surface of the fabrics.

It has now been found that the perfluoroalkyl compounds of the invention can impart excellent oil-repellent and anti-soiling properties to fibrous materials treated therewith. Aqueous and oily soils will not readily attach to the treated fibrous materials and, even if attached, can be readily and completely eliminated by conventional laundering techniques. Thus, the perfluoroalkyl compounds of the invention are useful as oil-repellent agents and anti-soiling agents. In addition, they are useful as plasticizers and also as intermediates for fluorine-containing polyurethanes.

The carboxylic ester compounds [IA] can be produced by reacting a perfluoroalkylpropylene oxide of the formula:

wherein Rf is as defined above with a reagent of the formula:

Q(COOH)$_m$    [III]

wherein Q and $m$ are each as defined above.

The epoxide [II] may be prepared, for instance, by adding radically a perfluoroalkyl iodide of the formula: RfI wherein Rf is as defined above to allyl alcohol and treating the resultant alcohol of the formula: RfCH$_2$CHICH$_2$OH wherein Rf is as defined above with an alkali hydroxide (e.g. sodium hydroxide, potassium hydroxide) in water to eliminate hydrogen iodide therefrom. Examples of the epoxide [II] are as follows:

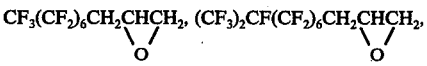

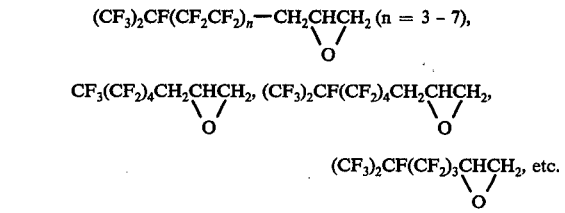

The reagent [III] is carboxylic acids having a basicity of not less than 2, and preferred examples are as follows:

(i) a dibasic carboxylic acid of the formula:

Q$_1$(COOH)$_2$ wherein Q$_1$ is a divalent hydrocarbon residue such as —(CH$_2$)$_p$— wherein $p$ is an integer of 1 to 4, —CH=CH— or —C$_6$H$_4$— (e.g. malonic acid, succinic acid, glutaric acid, maleic acid, fumaric acid, adipic acid, phthalic acid);

(ii) an acid having a basicity of more than 2 (e.g. pentane-1,3,3,5-tetracarboxylic acid, mellitic acid, pectinic acid, alginic acid, hemimellitic acid, trimellitic acid, benzenepentacarboxylic acid, citric acid, aconitic acid, trimesic acid, polyacrylic acid);

(iii) a dicarboxylic acid containing polyethylene oxide chain of the formula: HOOCAO(CH$_2$CH$_2$O)$_q$ACOOH wherein —ACOO— is —R'COO—, —COCH=CHCOO— or —COCH=CHCOO(CH$_2$CH- $_2$O)$_r$COCH=CHCOO— in which R' is a divalent hydrocarbon group and q and r are each an integer of not less than 1 (e.g. HOOCCH$_2$CH$_2$O(CH$_2$—CH$_2$O)$_n$CH$_2$CH$_2$COOH, HOOCCH$_2$O(CH$_2$CH$_2$O)$_n$CH$_2$COOH, HOOCCH=CHCOO(CH$_2$—CH$_2$O)$_n$COCH=CHCOOH, HOOCCH=CHCOO(CH$_2$CH$_2$O)$_n$COCH=CHCOO(CH$_2$CH$_2$O)$_n$—COCH=CHCOO(CH$_2$CH$_2$O)$_n$COCH=CHCOOH,

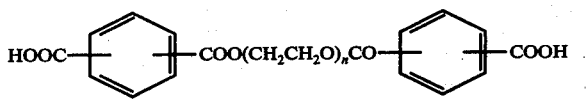

(n = 4–140)).

The reaction between the epoxide [II] and the carboxylic acid [IIIa] is representable by the formula:

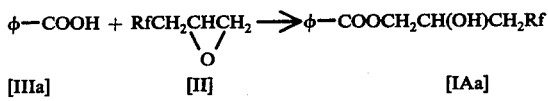

wherein φ is the residue of a carboxylic acid excluding —COOH therefrom and Rf is as defined above.

As the carboxylic acid [IIIa] is, in most cases, soluble in water and apt to be removed from the reaction mixture, it is preferred to be employed in a slightly excess amount. The epoxide [II] is normally liquid at room temperature, and the reaction may be carried out without using any solvent. The carboxylic acid [IIIa] has generally a melting point higher than 80° C, and the reaction is favorably carried out at a temperature higher than 80° C. The reaction rate is in general markedly suppressed at a temperature lower than 80° C, although it is more or less associated with the kind of the carboxylic acid [IIIa]. The addition of a base such as an alkali metal hydroxide (e.g. sodium hydroxide, potassium hydroxide) or a tertiary amine (e.g. triethylamine) as a catalyst to the reaction system may result in the acceleration of the reaction rate. The yield of the carboxylic ester compound [IAa] in the reaction is excellent and nearly quantitative.

Examples of the carboxylic ester compound [IAa] obtained by the reaction using the carboxylic acid [IIIa] include:

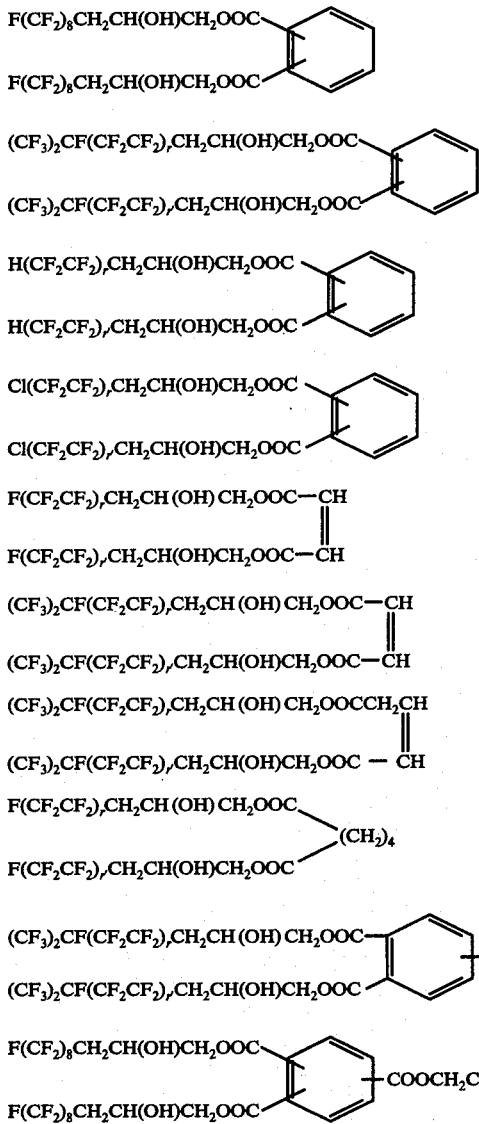

-continued

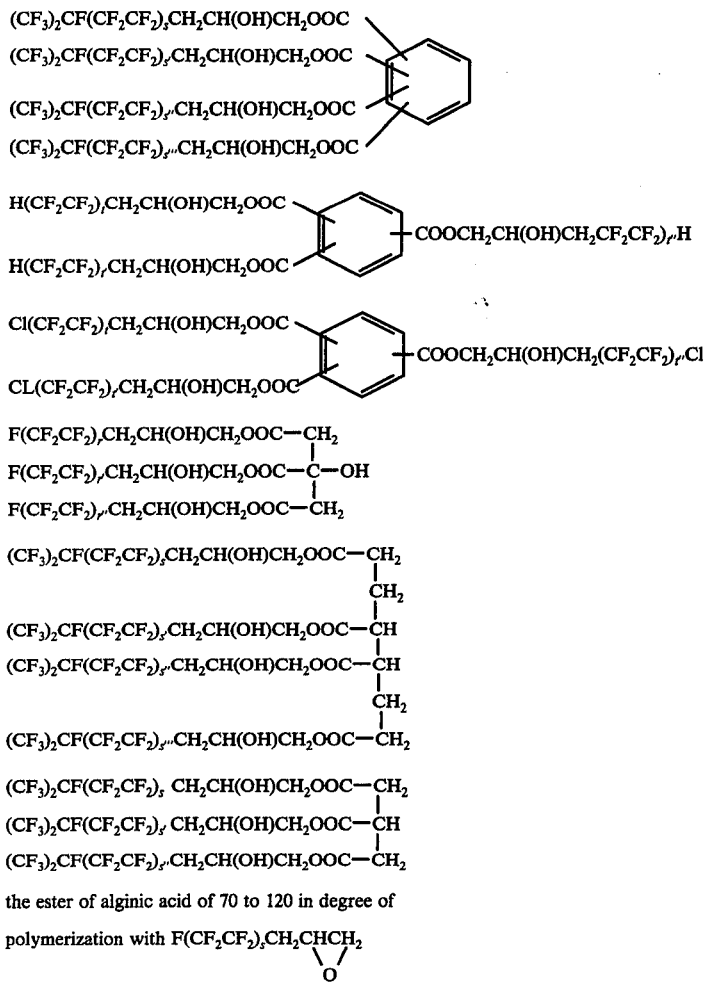

the ester of alginic acid of 70 to 120 in degree of polymerization with F(CF$_2$CF$_2$)$_s$CH$_2$CHCH$_2$
\O/ wherein r, r' and r" are each an integer of 2 to 10, s, s', s" and s''' are each an integer of 0 to 10 and t, t' and t" are each an integer of 3 to 20.

The amine compound [IB] can be produced by reacting a perfluoroalkylpropylene oxide of the formula:

RfCH$_2$CHCH$_2$      [II]
    \O/ wherein Rf is as defined above with a reagent of the formula:

Q'(NHR)$_{m'}$      [IV]

wherein R is a hydrogen atom or a group of the formula: —CH$_2$CH(OH)CH$_2$Rf, Rf being as defined above, and Q' and m' are each as defined above.

As the reagent [IV], there may be employed ammonia, a primary amine or a secondary amine.

Examples of the primary amine and the secondary amine are ethylamine, diethylamine, propylenediamine, hexamethylenediamine, pentaethylenehexamine, melamine, octadecylamine, hexamethylenetetramine, aniline, diethylenetriamine, triethylenetetramine, cyclohexylamine, benzylamine, benzylaniline and an amine containing polyethylene oxide chain of the formula: R"HNR'O(CH$_2$CH$_2$O)$_p$R'NHR" wherein R" is a hydrogen atom or an alkyl group and R' and p are each as defined above (e.g. H$_2$N(CH$_2$)$_3$O(CH$_2$CH$_2$O)$_n$(CH$_2$)$_3$NH$_2$, C$_2$H$_5$NH(CH$_2$)$_3$O(CH$_2$CH$_2$O)$_n$(CH$_2$)$_3$—NHC$_2$H$_5$, CH$_3$NH(CH$_2$)$_3$O(CH$_2$CH$_2$O)$_n$(CH$_2$)$_3$NHCH$_3$,

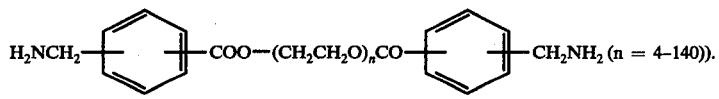

The reaction between the epoxide [II] and the primary amine [IVa] proceeds as follows:

φ'—NH$_2$ + RfCH$_2$CHCH$_2$ —→ φ'—NHCH$_2$CH(OH)CH$_2$Rf
 [IVa]         \O/  [II]                              [IBa]

φ'—NHCH$_2$CH(OH)CH$_2$Rf + RfCH$_2$CHCH$_2$ —→
         [IBa]                    \O/  [II]

-continued

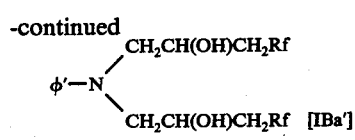
[IBa']

wherein φ' is the residue of a primary amine excluding —NH₂ therefrom and Rf is as defined above. Thus, the reaction of the epoxide [II] with the primary amine [IVa] in equimolar amounts affords the secondary amine [IBa] and, when the epoxide [II] is employed in two molar amount to one molar amount of the primary amine [IVa], there is obtained the tertiary amine [IBa']. The reaction between the epoxide [II] and the secondary amine [IVb] is represented by the formulae:

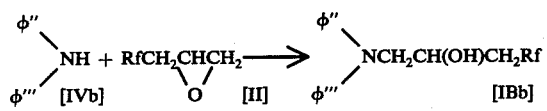

wherein φ" is the residue of a secondary amine excluding —NH—φ‴ therefrom, φ‴ is the residue of a secondary amine excluding —NH—φ" therefrom and Rf is as defined above. In place of the primary amine [IVa] or the secondary amine [IVb], there may be used ammonia [IVc], which is reacted with the epoxide [II] as follows:

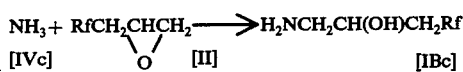

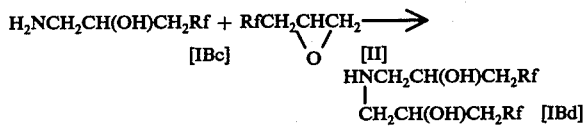

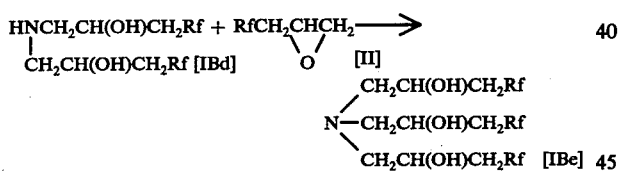

All the above reactions are usually effected by treating the epoxide [II] with the primary amine [IVa], the secondary amine [IVb] or ammonia [IVc] in a slightly excess amount at a temperature from 30° to 150° C, preferably from 80° to 100° C. The use of a solvent is not always needed. If employed, the use of an inert organic solvent such as fluoroalknes is recommended for controlling the elevation of temperature caused by generation of heat. In general, the presence of water in the reaction system is unfavorable, and its amount should be suppressed to not more than 10% by weight. The reactions can be promoted by the use of a tertiary amine (e.g. triethylamine). The reactions are normally completed in 30 minutes to 10 hours to give the perfluoroalkyl compound [IBa] — [IBe] in nearly quantitative yields. The thus obtained perfluoroalkyl compound [IBa] — [IBe] may be further converted into its acid addition salt by treatment of the former with an organic or inorganic acid usually at a temperature from room temperature to 100° C, if desired, in an inert organic solvent such as fluoroalkanes. This conversion is advantageously carried out immediately after completion of the reaction between the epoxide [II] and the primary amine [IVa], the secondary amine [IVb] or ammonia [IVc], i.e. without the isolation of the produced perfluoroalkyl compound [IBa] — [IBe] from the reaction mixture. The perfluoroalkyl compound [IBa] — [IBe] itself is a liquid or solid which is insoluble in water, whereas most of its acid-addition salts are soluble in water. Both are utilizable for the object of this invention.

The produced perfluoroalkyl compound [IBa] — [IBe] is fallen in one of the following formulae:

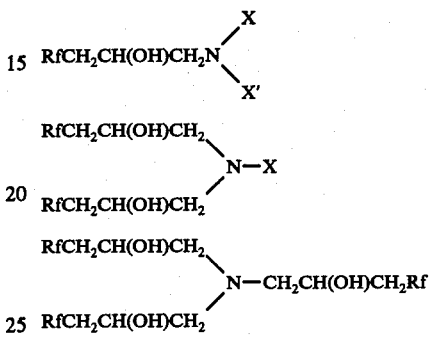

wherein X and X' are each a hydrogen atom or a hydrocarbon group bearing or not one or more substituents. Specific examples are as follows:

$CF_3(CF_2)_6CH_2CH(OH)CH_2N(C_2H_5)_2$
$CF_3(CF_2)_6CH_2CH(OH)CH_2N(CH_3)_2$
$CF_3(CF_2)_6CH_2CH(OH)CH_2NH(CH_2)_4NHCH_2CH(OH)CH_2(CF_2)_4CF_3$
$(CF_3)_2CF(CF_2)_6CH_2CH(OH)CH_2NH_2$

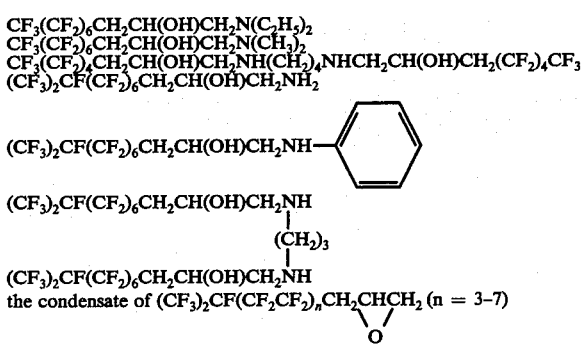

the condensate of $(CF_3)_2CF(CF_2CF_2)_nCH_2CHCH_2$ (n = 3–7)
\O/
with diethylenetriamine As stated above, the perfluoroalkyl compound [IA] or [IB] (including the acid addition salt) have oleophobic and anti-soiling properties. Based on such properties, they are used for treatment of fibrous materials.

On treating fibrous materials with the perfluoroalkyl compound [IA] or [IB] (including the acid addition salt), the active ingredient is dissolved or dispersed in a suitable solvent to make 0.05 to 5% by weight concentration, the fibrous materials are immersed therein and the wet materials are dried in atmosphere or while heating at 80° to 150° C for 30 seconds to 10 minutes.

As the solvent, the use of an organic solvent having a boiling point from 30° to 150° C, particularly from 35° to 100° C, is preferred. Specific examples of such organic solvent are fluoroalkanes (e.g. trichlorotrifluoroethane, dichlorotetrafluoroethane), ketones (e.g. acetone, methyl ethyl ketone), esters (e.g. ethyl acetate), fluorine-containing cyclic compounds (e.g. benzotrifluoride), etc. For dilution of these solvents, there may be also used benzene, petroleum ether, xylene or the like.

From the economical viewpoint, it is advantageous to make up an aqueous dispersion. Thus, the active ingredient is dispersed in water in the presence of an appropriate emulsifier by conventional operations. Examples of the emulsifier are anionic surfactants (e.g. sodium dodecylbenzenesulfonate, $C_7F_{15}COONa$), non-ionic surfactants (e.g. polyoxyethylenealkyl phenyl ether, polyoxyethylene amyl ester, sorbitan fatty acid ester), cationic surfactants (e.g. quaternary ammonium salts), etc.

The textile fabrics treated with the anti-soiling treatments of this invention are quite excellent in repellency to stains, stain-removing actions, prevention of soil redeposition during laundering and durability to laundering and show very favorable appearance.

The perfluoroalkyl compound [IA] or [IB] (including the acid addition salt) is also used for the separation of water and oil (e.g. kerosene, sesame oil, heavy oil, machine oil, watch oil, refrigerator oil, hexane, heptane, octane, cyclohexane) from their mixture. For instance, porous materials such as paper, woven fabric, non-woven fabric and asbestos are treated with the active ingredient dissolved or dispersed in water or organic solvents, if necessary, by the aid of surfactants so that the porous materials are imparted oil-repellency and allows only the passing of water therethrough.

The perfluoroalkyl compound [IA] or [IB] (including the acid addition salt) may be also employed in combination with any water-phobic agent. In such case, the materials treated with them are imparted both oil-repellency and water-repellency. Examples of the water-phobic agent are the polymers of the fluorine-containing vinylcarboxylic esters of the formula: $RfCH_2CH(OH)CH_2OOCCR_3=CH_2$ wherein $R_3$ is a hydrogen atom or a methyl group. The vinylcarboxylic esters may be produced, for instance, by reacting the epoxide of the formula:

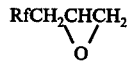

or the diol of the formula: $RfCH_2CH(OH)CH_2OH$ with acrylic acid or methacrylic acid. The ratio by weight of the perfluoroalkyl compound [IA] or [IB] and the vinylcarboxylic ester is 9:1 - 1:9, favorably 5:1 - 1:5. On treatment, these active ingredients are employed in the form of solution or dispersion in water or organic solvents, if necessary, by the aid of surfactants.

In addition to the above uses, the perfluoroalkyl compound [IA] or [IB] (including the acid addition salt) may be used as plasticizers or intermediates for the synthesis of polyurethanes. For instance, the diol of the formula: $[RfCH_2CH(OH)CH_2OOC]_2Y$ wherein Y is a hydrocarbon group bearing or not one or more substituents or its mixture with an active hydrogen-containing material such as ethyleneglycol adipate, propyleneglycol adipate, condensates of ω-hydroxyhexanoate or glycerol adipate is polymerized with a diisocyanate of the formula: $OCNY'NCO$ wherein Y' is a hydrocarbon group (e.g. 2,4- or 2,6-tolylenediisocyanate, 3,3'-bitolylene-4,4'-diisocyanate, diphenylmethane-4,4'-diisocyanate, 3,3'-dimethyldiphenylmethane-4,4'-diisocyanate, methaphenylenediisocyanate, triphenylmethanetriisocyanate, 2,4-tolylenediisocyanate dimer, hexamethylenediisocyanate, naphthylene-1,5-diisocyanate). The polymerization is effected at a temperature from room temperature to 150° C, preferably in the presence of a small amount of a catalytic substance (e.g. ethylenediamine, triethylamine, triethylenediamine, dimethylethanolamine, bis(diethylethanolamine) adipate, N,N-dimethylcyclohexylamine, dibutyl tin laurate, dibutyl tin di(2-ethylhexanoate), stannous 2-ethylcaproate, stannous oleate). The ratio of the perfluoroalkyl compound [IA] or [IB] and the diisocyanate to be used may be appropriately decided on the kind of the polyurethane to be required. The thus obtained polyurethane has oleophobic and anti-soiling properties and possesses a wide variety of uses, e.g. the use as coating materials, the use as additives to painting, etc.

Practical and presently preferred embodiments of the invention are illustratively shown in the following Examples. In these Examples, parts and percent are by weight unless otherwise indicated. Further, various properties such as water-repellency, oil-repellency, stain-repellency, stain-removability and anti-soil redeposition in the following Examples are determined by the methods as described below:

1. Water-repellency

Measurement is effected according to A.A.T.C.C. Standard Test Method 22-1952.

2. Oil-repellency

Measurement is effected according to A.A.T.C.C. Standard Test Method 118-1966T.

3. Stain removabilty

A test cloth is put on a blotting paper extended evenly, and 5 drops of liquid paraffin in admixture with purple dye "Waxoline Purple AS" (manufactured by I.C.I., England) are added dropwise onto one place of the test cloth, which is covered with a polyethylene film. The test cloth is pressed by 2.27 kg of poise for a minute, which is removed. The excess of the liquid paraffin is wiped off with a cotton cloth. The test cloth is allowed to stand for 12 hours and laundered.

Laundering is effected with a drum side-rolling automatic washing machine (manufactured by Sakata Kiko Co., Ltd.). To cloths (300 g) including the test cloth, there are added water (15 L) warmed at 45° C and a conventional cleaning material (e.g. "Kao Big" (made by Kao Soap Co., Ltd.)) (38 g). The resultant mixture is laundered for 10 minutes and washed with water for 2 minutes three times. Liquid paraffin-removing degrees are judged by the decolored degree of the purple color. Standard of the decolorization is as follows: same color as that of unlaundered cloth: 1.0; completely decolored case: 5.0; grades between them are judged respectively.

4. Anti-soil redeposition

Soil redeposition bath (150 ml) having the composition as defined in the following table is adjusted, stirred at 50° C well, and 6 sheets of test cloth (6 × 6 cm) and 15 steel balls are added to the bath. Soiling of the test cloth is effected by turning Launder-O-Meter at 50° C for 20 minutes. The soiled cloth is washed with water for 10 minutes and air-dried.

The reflectance of the test cloth is measured by using a photometer and the rate of soil redeposition is calculated by the following equation:

$$\text{Rate of soil redeposition} = \frac{\text{Reflectance of unsoiled cloth} - \text{Reflectance of soiled cloth}}{\text{Reflectance of unsoiled cloth}} \times 100$$

Composition of soil redeposition bath (%, by weight)

| | |
|---|---|
| Cleaning material (0.18 %) | |
| Sodium dodecylbenzenesulfonate | 0.045 % |
| Sodium tripolyphosphate | 0.045 % |
| Sodium sulfate | 0.09 % |
| Particulate soil (0.722 %) | |
| Carbon black HAF "Shoblack-O" (made by Showa Denko K.K.) | 0.0144 % |
| Ferric oxide | 0.0036 % |
| Iron Oxide "Yellow 920" | |

-continued

| | |
|---|---|
| Rate of soil redeposition = (Reflectance of unsoiled cloth − Reflectance of soiled cloth) / Reflectance of unsoiled cloth × 100 | |
| Composition of soil redeposition bath (%, by weight) | |
| (made by Bayer A.G.) | 0.0072 % |
| Cellulose powder | 0.144 % |
| Bentonite (clay) | 0.552 % |
| Fatty soil (0.063 %) | |
| Stearic acid | 0.0052 % |
| Oleic acid | 0.0052 % |
| Triolein | 0.0052 % |
| Tristearin | 0.0052 % |
| Stearyl alcohol | 0.0052 % |
| Oleyl alcohol | 0.0052 % |
| Solid paraffin (M.P. 58 to 60° C) | 0.0104 % |
| Cholesterol | 0.0010 % |
| Sodium chloride | 0.0208 % |

Part A:-

EXAMPLE 1

In a 250 ml volume flask equipped with a thermometer, a stirrer and a cooler, $$(CF_3)_2CF(CF_2)_4CH_2CHCH_2 \underset{O}{\diagdown\diagup}$$

(127.8 g, 0.30 mol), itaconic acid (19.5 g, 0.15 mol), triethylamine (6 g) and hydroquinone (1 g) are charged, and the mixture is stirred at 100° to 110° C for 6 hours. After confirming the complete consumption of the starting epoxide by gas chromatography, the reaction mixture is distilled under atmospheric pressure to remove triethylamine whereby dark brown solid (153 g) is obtained. The solid is washed with 3% KOH solution at 80° to 85° C to eliminate unreacted itaconic acid and, after washing well with pure wter, recrystallized from ethyl acetate (500 ml) to give as pale yellow solid (130 g, 0.13 mol) the ester of the formula:

$$(CF_3)_2CF(CF_2)_4CH_2\underset{OH}{C}HCH_2OOC$$
$$\diagdown$$
$$C=CH_2$$
$$\diagup$$
$$(CF_3)_2CF(CF_2)_4CH_2\underset{OH}{C}HCH_2OOCCH_2$$

Elementary analysis. Calcd.: F, 58.04%; C, 29.32%; O, 9.78%. Found: F, 56.88%; C, 30.03%; O, 9.53%.

Infrared absorption spectrum: 3500 (OH), 1720

$$(-\underset{O}{\overset{\|}{C}}-O-),$$

1150–1300 and 980 (fluorinated alkyl), 1650 (—C=C—) cm$^{-1}$.

EXAMPLE 2

In a 250 ml volume flask equipped with a thermometer, a stirrer and a cooler, $$(CF_3)_2CF(CF_2CF_2)_nCH_2CHCH_2 \underset{O}{\diagdown\diagup}$$

[n = 3–7; consisting of 50% of the compound (n = 3), 31% of the compound (n = 4), 12% of the compound (n = 5), 4% of the compound (n = 6) and 3% of the compound (n = 7)] (125 g, 0.2 mol), maleic acid (11.6 g, 0.1 mol), triethylamine (4 g) and hydroquinone (0.5 g) are charged, and the mixture is stirred at 85° to 90° C for 6 hours. After confirming the complete consumption of the starting epoxide by gas chromatography, the reaction mixture is distilled under atmospheric pressure to remove triethylamine whereby dark brown viscous material (137 g) is obtained. The solid is recrystallized from ethyl acetate (300 ml) to give the ester as plase yellow wax solid (134.9 g, 0.091 mol). M.P. 78° to 83° C.

Infrared absorption spectrum: 3350 (OH), 1725

$$(-\underset{O}{\overset{\|}{C}}-O-),$$

1150–1250 and 980 (fluorinated alkyl) cm$^{-1}$.

EXAMPLE 3

As in Example 1, $$(CF_3)_2CF(CF_2CF_2)_nCH_2CHCH_2 \underset{O}{\diagdown\diagup}$$

[n = 3–7, consisting of 50% of the compound (n = 3), 31% of the compound (n = 4), 12% of the compound (n = 5), 4% of the compound (n = 6) and 3% of the compound (n = 7)] (95 g, 0.151 mol) is reacted with phthalic acid (12.55 g, 0.0755 mol) in the presence of potassium hydroxide (3 g) at 110° to 130° C for 1.5 hours. The product is decolorized with active carbon in trichlorotrifluoroethane to give the ester as white solid (102 g, 0.0715 mol). M.P. 66° to 70° C.

EXAMPLE 4

As in Example 1, $$H(CF_2)_6CH_2CHCH_2 \underset{O}{\diagdown\diagup}$$

(85.6 g, 0.239 mol) is reacted with terephthalic acid (19.8 g, 0.119 mol) in the presence of triethylamine (6.0 g) at 110° to 120° C for 3 hours to give the ester (96 g, 0.108 mol).

EXAMPLE 5

As in Example 1, $$(CF_3)_2CF(CF_2)_4CH_2CHCH_2 \underset{O}{\diagdown\diagup}$$

(127.8 g, 0.30 mol) is reacted with citric acid (19.2 g, 0.15 mol) in the presence of triethylamine (2 g) at 100° to 110° C for 6 hours. Recrystallization of the product from ethyl acetate affords as pale yellow solid (128 g) the ester of the formula:

$$(CF_3)_2CF(CF_2)_4CH_2\underset{OH}{C}HCH_2OOC-CH_2$$
$$(CF_3)_2CF(CF_2)_4CH_2\underset{OH}{C}HCH_2OOC-\underset{OH}{C}-OH$$
$$(CF_3)_2CF(CF_2)_4CH_2\underset{OH}{C}HCH_2OOC-CH_2$$

M.P. 35° to 37° C.

Elementary analysis. Calcd.: F, 58.17%; C, 29.39%; O, 10.88%. Found: F, 57.95%; C, 29.78%; O, 11.03%.

Infrared absorption spectrum: 3500 (OH), 1720

$$(-\underset{\underset{O}{\|}}{C}-O-),$$

1150–1300 and 980 (fluorinated alkyl) cm$^{-1}$.

EXAMPLE 6

As in Example 1,

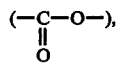
$$(CF_3)_2CF(CF_2CF_2)_nCH_2\underset{O}{\underset{\diagdown\;\diagup}{CHCH_2}}$$

[n = 3–9; consisting of 50% of the compound (n = 3), 31% of the compound (n = 4), 12% of the compound (n = 5), 4% of the compound (n = 6) and 3% of the compound (n = 7)] (187 g) is reacted with trimellitic acid (21 g) in the presence of triethylamine (2 g) at 120° to 130° C for 4 hours. Recrystallization of the product from ethyl acetate affords the ester as pale yellow solid (163 g). M.P. 79° to 83° C.

Infrared absorption spectrum: 3350 (OH), 1725

$$(-\underset{\underset{O}{\|}}{C}-O-),$$

1150–1250 and 980 (fluorinated alkyl) cm$^{-1}$.

EXAMPLE 7

As in Example 1,

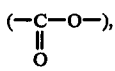
$$(CF_3)_2CF(CF_2CF_2)_nCH_2\underset{O}{\underset{\diagdown\;\diagup}{CHCH_2}}$$

[n = 3–9; consisting of 50% of the compound (n = 3), 31% of the compound (n = 4), 12% of the compound (n = 5), 4% of the compound (n = 6) and 3% of the compound (n = 7)] (95 g, 0.151 mol) is reacted with trimellitic acid (8.7 g, 0.0252 mol) in the presence of potassium hydroxide at 110° to 130° C for 3.5 hours. The product is decolorized with active carbon in trichlorotrifluoroethane to give the ester as pale brown solid (98 g). M.P. 120° to 125° C.

EXAMPLE 8

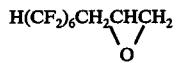
$$H(CF_2)_6CH_2\underset{O}{\underset{\diagdown\;\diagup}{CHCH_2}}$$

(85.6 g), 0.239 mol) is reacted with alginic acid (degree of polymerization, 70 to 130; 42 g) in the presence of potassium hydroxide (2 g) at 110° to 120° C for 6 hours. The pale brown product (125 g) is dissolved in trifluorotrichloroethane, and the resultant solution is portionwise added to water. The precipitate is collected to give the ester as white solid (80 g). In the infrared absorption spectrum, no absorption on a carboxyl group is seen and the absorption of ester is found.

EXAMPLE 9

As in Example 8,

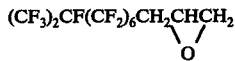
$$(CF_3)_2CF(CF_2)_6CH_2\underset{O}{\underset{\diagdown\;\diagup}{CHCH_2}}$$

(21.6 g) is reacted with polyacrylic acid (degree of polymerization, 300 to 500; 30 g) in the presence of triethylamine (1 g) to give the ester as pale brown solid (50 g). By the infrared absorption spectrum, it is confirmed that almost all of the carboxyl groups present in the polyacrylic acid are esterified.

EXAMPLE 10

In a 200 ml volume flask equipped with a thermometer, a stirrer and a cooler, HOOCCH$_2$CH$_2$O(CH$_2$CH$_2$O)$_n$CH$_2$CH$_2$COOH (n = 4–140; average molecular weight, ca. 790) (85 g), (CF$_3$)$_2$CF-

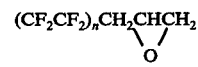
$$(CF_2CF_2)_nCH_2\underset{O}{\underset{\diagdown\;\diagup}{CHCH_2}}$$

(n = 3–9; average molecular weight, ca. 620) (124 g) and triethylamine (2.0 g) are charged, and the mixture is heated at 90° to 100° C for 4 hours. After confirming the complete consumption of the epoxide by gas chromatography, the reaction mixture is cooled and washed with water to give the condensate.

The condensate (50 g), an emulsifier (8 g) obtained by the reaction between dimethyldodecylamine and acetic acid in a molar ratio of 1:3, polyethylene glycol octyl nonyl ether (H.L.B. 18.5) (1.5 g) and ethylene glycol (2.5 g) are charged in a homogenizer and treated for 10 minutes. After addition of hot water (25 g) of 80° C, the mixture is treated for 10 minutes. Hot water (25 g) of 80° C is further added, and the resultant mixture is treated for 20 minutes to give a dispersion of high stability.

The dispersion (1.3 g) is diluted with pure water (98.7 g), and 6 sheets of cloth made of polyethylene terephthalate fiber and cotton fiber (65:35) are immersed therein for 1 minute and dried at 80° C for 20 minutes. Three sheets of them are subjected as such to the tests for oil-repellency, stain removability and anti-soil redeposition. Other three sheets are laundered and then subjected to the tests as above. The results are shown in the following table:

Table 1

| | Oil-repellency | Stain removability | Anti-soil redeposition |
|---|---|---|---|
| Before laundering | 7 | 5 | 10 |
| After laundering | 6 | 4.5 | 8.5 |

EXAMPLE 11

As in Example 10, HOOCCH=CHCOO(CH$_2$CH$_2$O)$_n$OCCH=CHCOO—(CH$_2$CH$_2$O)$_n$OCCH=CHCOOH (n = 4–140; average molecular weight, ca. 4000) (420 g),

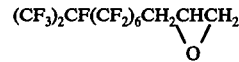
$$(CF_3)_2CF(CF_2)_6CH_2\underset{O}{\underset{\diagdown\;\diagup}{CHCH_2}}$$

(106 g) and triethylamine (2.3 g) are reacted to give the condensate. The condensate is treated in a homogenizer to give a yellowish brown emulsion having a solid concentration of 35%. The emulsion is diluted with water to make 1% concentration, and a cloth made of polyethylene terephthalate is immersed therein and dried. The oil-repellency, stain removability and anti-soil redeposition of the cloth are shown in the following table:

Table 2

|  | Oil-repellency | Stain removability | Anti-soil-redeposition |
|---|---|---|---|
| Before laundering | 7 | 5 | 10 |
| After laundering | 6 | 4.5 | 8 |

EXAMPLE 12

In a 500 ml volume flask, [(CF$_3$)$_2$CF(CF$_2$CF$_2$)$_n$CH$_2$CH(OH)—

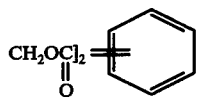

[n = 3-9; consisting of 50% of the compound (n = 3), 31% of the compound (n = 4), 12% of the compound (n = 5), 4% of the compound (n = 6) and 3% of the compound (n = 7-9)] (175 g, 0.15 mol) and toluene (300 ml) are charged, and tolylenediisocyanate (26 g, 0.15 mol) and triethylamine (0.5 g) are added thereto. the resultant mixture is heated while refluxing for 1 hour and the solvent is removed by distillation under reduced pressure to give the polyurethane as yellowish brown, transparent resin (198 g). The polyurethane is not softened even at 120° C and can be broken into small pieces when struck with a wooden hammer.

A cloth made of polycapramide fiber is immersed in 1% solution of the polyurethane in a mixture of 90% of trifluorotrichloroethane and 10% of acetone and dried at room temperature. The cloth shows 10 in water-repellency and 10 in oil-repellency.

EXAMPLE 13

A mixture of

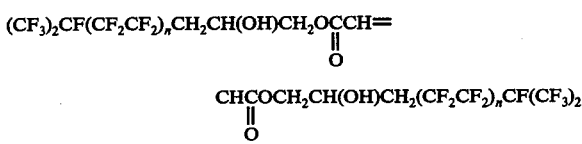

(n = 3-8) (6.8 g, 0.0045 mol), tolylenediisocyanate (0.8 g, 0.0045 mol) and triethylamine (0.1 g) is heated at 60° C while stirring and then allowed to stand at room temperature for 3 days to give the polyurethane as yellowish brown, transparent resin. The polyurethane is not softened even at 120° C and can be broken into small pieces when struck with a wooden hammer.

A cloth made of cotton fiber is immersed in 1% solution of the polyurethane in a mixture of 90% of trifluoroethane and 10% of acetone and dried at room temperature. The cloth shows 9 in water-repellency and 10 in oil-repellency.

EXAMPLE 14

The ester of the formula: (CF$_3$)$_2$CF(CF$_2$)$_4$CH$_2$CH(OH)—CH$_2$OOCCH=CH-COOCH$_2$CH(OH)CH$_2$(CF$_2$)$_4$CF(CF$_3$)$_2$ (1 g) is dissolved in acetone (200 ml), the resultant solution is admitted in a sprayer for aerosol and a mixture (200 ml) of dichlorodifluoromethane and trichlorofluoromethane (75:25 by weight) is charged therein to prepare an aerosol type composition.

The aerosol type composition is sprayed on a filter paper, and the paper is dried at room temperature for several minutes. When a mixture of water and kerosene is placed on the paper, only water passes through at once and kerosene is retained thereon. Even after 2 days, kerosene does not pass through the paper. The passed water is transparent and odorless and contains no kerosene.

EXAMPLE 15

The ester of the formula: (CF$_3$)$_2$CF(CF$_2$)$_4$CH$_2$CH(OH)—CH$_2$OOCCH=CH-COOCH$_2$CH(OH)CH$_2$(CF$_2$)$_4$CF(CF$_3$)$_2$ (1 g) is dissolved in acetone (400 ml). A filter paper is immersed in the resultant solution and dried at room temperature for 10 minutes. The paper has the same appearance as an untreated filter paper but can retain kerosene, sesame oil and n-decane thereon for more than 1 day. Water passes through the paper with great ease.

EXAMPLE 16

The ester of the formula: (CF$_3$)$_2$CF(CF$_2$CF$_2$)$_n$CH$_2$CH(OH)—CH$_2$OOCCH=CHCOOCH$_2$CH(OH)CH$_2$(CF$_2$CF$_2$)$_n$CF(CF$_3$)$_2$ [n = 3-7; consisting of 54% of the compound (n = 3), 28% of the compound (n = 4), 12% of the compound (n = 5), 4.5% of the compound (n = 6) and 1.5% of the compound (n = 7); M.P. 82° C] (1 g) is dissolved in acetone (100 ml). A porous sheet of asbestos containing a binder of polyvinyl alcohol is treated with the resultant solution and dried at room temperature. When a mixture of water and n-octane is placed on the sheet, only water passes through the same.

EXAMPLE 17

The ester of the formula:

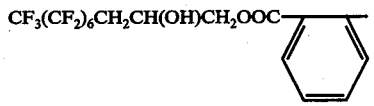

COOCH$_2$CH(OH)CH$_2$(CF$_2$)$_6$CF$_3$ (1 g) and the ester of the formula:

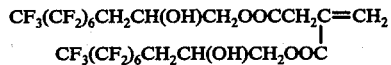

(1 g) are dissolved in acetone (400 ml). When a mixture of water and machine oil is placed on the cloth of polyvinyl alcohol treated with the resultant solution, water passes through the same but machine oil does not. Thus, the mixture is separated into water and machine oil by the aid of such cloth.

EXAMPLE 18

An end of a cylinder is covered with a sheet of asbestos obtained in Example 16 and the other end is covered with a non-fabric cloth made of polytetrafluoroethylene. A dry cleaning waste liquor consisting of trichloroethylene and water is introduced into the cylinder at the central part through a pump so that water is obtained from the end covered with the asbestos sheet and trichloroethylene from the other end. No material change in the separation effect of the cylinder is seen even after used for 7 hours per day in a period of 1 month.

EXAMPLE 19

Six sheets of a cloth made of polyethylene terephthalate fiber and of rayon fiber (80:20) are immersed in a solution of the ester of the formula: $(CF_3)_2CF(CF_2CF_2)_nCH_2CH(OH)-CH_2OOCCH=CHCOOCH_2CH(OH)CH_2(CF_2CF_2)_nCF(CF_3)_2$ [$n$ = 3–9; consisting of 50% of the compound ($n$ = 3), 31% of the compound ($n$ = 4), 12% of the compound ($n$ = 5), 4% of the compound ($n$ = 6) and 3% of the compound ($n$ = 7–9)] (1 g) in a mixture of acetone (10 ml) and trichlorotrifluoroethane (190 ml) and dried at room temperature for about 1 hour. Three sheets of them are subjected as such to the tests for oil-repellency, stain removability and anti-soil redeposition. Other three sheets are laundered and then subjected to the tests as above. The results are shown in the following table:

Table 3

|  | Oil-repellency | Stain removability | Anti-soil redeposition |
| --- | --- | --- | --- |
| Before laundering | 7 | 4.5 | 9 |
| After laundering | 6 | 4 | 8 |

EXAMPLE 20

Fabrics made of polyethylene terephthalate fiber and of polycapramide fiber are immersed in a solution of the ester of the formula: $(CF_3)_2CF(CF_2CF_2)_nCH_2CH(OH)CH_2OOCCH=CHCOOCH_2CH(OH)CH_2(CF_2CF_2)_nCF(CF_3)_2$ [$n$ = 3–9; consisting of 50% of the compound ($n$ = 3), 31% of the compound ($n$ = 4), 12% of the compound ($n$ = 5), 4% of the compound ($n$ = 6) and 3% of the compound ($n$ = 7–9)] (1 part by weight) in a mixture (100 parts by volume) of acetone and trichlorotrifluoroethane (5:95 in volume ratio), dried in atmosphere and subjected to the tests for oil-repellency, stain removability and anti-soil redeposition. The results are shown in the following table:

Table 4

|  |  | Oil-repellency | Stain removability | Anti-soil redeposition |
| --- | --- | --- | --- | --- |
| Polyethylene terephthalate fiber | Before laundering | 7 | 4.5 | 8 |
|  | After laundering | 7 | 4.0 | 7 |
| Polycapramide fiber | Before laundering | 7 | 4.5 | 8 |
|  | After laundering | 7 | 4.5 | 7 |

The use of an aqueous dispersion of the said ester (1 g) in a mixture of sodium dodecylbenzenesulfonate (0.25 g), acetone (0.6 g) and water (98.15 g) in place of the above employed treating solution imparts also the same advantageous properties as above to fabrics.

The results of the tests carried out using known treating agents for fabrics made of polyethylene terephthalate fiber are shown in the following table:

Table 5

|  |  | Oil-repellency | stain removability | Anti-soil redeposition |
| --- | --- | --- | --- | --- |
| Polymer of perfluoroalkanesulfonyl acrylamide | Before laundering | 7 | 2 | 50 |
|  | After laundering | 7 | 2 | 67 |
| Copolymer of ethyl acrylate and acrylic acid | Before laundering | 0 | 4.5 | 11 |
|  | After laundering | 0 | 3 | 12 |

EXAMPLE 21

Cloths made of polyethylene terephthalate fiber and cotton fiber (65:35) are immersed in a solution of one of the following compounds:

(a) Terephthalic acid diester

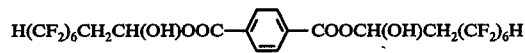

(b) Itaconic acid diester

(c) Adipic acid diester

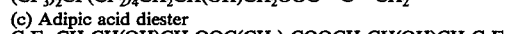

(1 g) in a mixture (100 g) of 5% by volume of acetone and 95% by volume of trichlorotrifluoroethane, dried in atmosphere and subjected to the tests for oil-repellency, stain removability and anti-soil redeposition. The results are shown in the following table:

Table 6

|  |  | Oil-repellency | Stain removability | Anti-soil redeposition |
| --- | --- | --- | --- | --- |
| Terephthalic acid diester | Before laundering | 4 | 4 | 15 |
|  | After laundering | 4 | 4 | 16 |
| Itaconic acid diester | Before laundering | 4 | 3.5 | 18 |
|  | After laundering | 3 | 3 | 18 |
| Adipic acid diester | Before laundering | 7 | 4.5 | 8 |
|  | After laundering | 7 | 4 | 8 |

EXAMPLE 22

The ester of the formula: $(CF_3)_2CF(CF_2CF_2)_nCH_2CH(OH)-CH_2OOCCH=CH_2$ [$n$ = 3–7; consisting of 54% of the compound ($n$ = 3), 28% of the compound ($n$ = 4), 12% of the compound ($n$ = 5), 4.5% of the compound ($n$ = 6) and 1.5% of the compound ($n$ = 7)] is polymerized using $C_{13}H_{27}N(CH_3)_2$· acetate as an emulsifier, and the resultant polymer is adjusted to a 15% aqueous emulsion (hereinafter referred to as "Emulsion I").

The ester of the formula: $(CF_3)_2CF(CF_2CF_2)_nCH_2CH(OH)-CH_2OOCCH=CHCOOCH_2CH(OH)CH_2(CF_2CF_2)_nCF(CF_3)_2$ [$n$ = 3–7; consisting of 54% of the compound ($n$ = 3), 28% of the compound ($n$ = 4), 12% of the compound ($n$ = 5), 4.5% of the compound ($n$ = 6) and 1.5% of the compound ($n$ = 7); M.P. ca. 82° C] is emulsified with $C_{12}H_{25}N(CH_3)_2$ acetate to prepare 15% aqueous emulsion (hereinafter referred to as "Emulsion II").

Emulsion I and Emulsion II are mixed in ratios as shown in the following table, and the resultant mixture is diluted to prepared a mixture bath of emulsion. Into the mixture bath, broad fabrics made of polyethylene terephthalate fiber and cotton fiber are immersed, squeezed to a pick-up of 70% with a mangle, dried at 80° C for 10 minutes and heated at 150° C for 5 minutes. Water-repellency, oil-repellency, stain removability and anti-soil redeposition of the thus treated fabrics are measured. The results are shown in the part (a) of the table.

Besides, the treated fabrics are laundered and then subjected to the tests as above mentioned. The results are shown in the part (b) of the table.

At the same time, the above treatments are effected by the method of using the above prepared mixture bath (hereinafter referred to as "Prescription A"), the method of using the same bath in mixture with 0.2 % ammonium chloride for the total amount of fluorocarbons (hereinafter referred to as "Prescription B") and the method of using the said mixture bath in admixture with 1.25% carbamate treating agent "Permafresh OHM" (made by Dainippon Ink Chemical Industry CO., Ltd.) and 0.6% zinc nitrate (hereinafter referred to as "Prescription C").

ingredient a block copolymer of $C_8F_{17}SO_2N(C_2H_5)CH_2CH_2OOCCH=CH_2$ and $CH_2=CClCH=CH_2$. The commercially available water-repellant is a composition containing as the main ingredient $C_{17}H_{35}CONHCH_2OH$.

EXAMPLE 23

As in Example 22, a 1:1 mixture of a 15% aqueous emulsion of $CF_3CF_2(CF_2CF_2)_nCH_2CH(OH)CH_2OOCCH=CH_2$ [$n = 3$-$7$; consisting of 54% of the compound ($n = 3$), 28% of the compound ($n = 4$), 12% of the compound ($n = 5$), 4.5% of the compound ($n = 6$) and 1.5% of the compound ($n = 7$)] with $C_{18}H_{37}N(CH_3)_2$. acetate as an emulsifier and a 15% aqueous emulsion of $CF_3CF_2-$

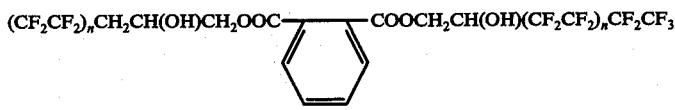

[$n = 3$-$7$; consisting of 54% of the compound ($n = 3$), 28% of the compound ($n = 4$), 12% of the compound ($n = 5$), 4.5% of the compound ($n = 6$) and 1.5% of the compound ($n = 7$); M.P. 67° to 70° C] with

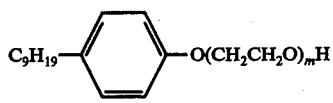

($m = 15$ in average) as an emulsifier is applied to fabrics made of polyethylene terephthalate fiber. When treated Table 7

| Ratio of Emulsions I/II (volume ratio) | Total solid fluoro-carbon content in bath (weight %) | Pre scrip-tion | (a) Before laundering | | | | (b) After laundering | | | |
|---|---|---|---|---|---|---|---|---|---|---|
| | | | Water-repel-lency | Oil-repel-lency | Stain remov-ability | Anti-soil redeposi-tion | Water-repel-lency | Oil-repel-lency | Stain remov-ability | Anti-soil redeposi-tion |
| I alone | 0.4 | A | 80 | 5 | 4 | 15 | 70 | 3 | 4 | 18 |
| | 0.4 | B | 100 | 6 | 3.5 | 17 | 70 | 2 | 3 | 15 |
| | 0.4 | C | 100 | 6 | 8.5 | 18 | 80 | 4 | 3 | 18 |
| II alone | 0.4 | A | 50⁻ | 7 | 5 | 8 | 0 | 6 | 5 | 9 |
| | 0.4 | B | 50 | 7 | 4.5 | 8 | 0 | 7 | 4.5 | 9 |
| | 0.4 | C | 50 | 7 | 4.5 | 9 | 50⁻ | 7 | 4.5 | 9 |
| 1/1 | 0.4 | A | 70 | 7 | 5 | 7 | 50 | 7 | 5 | 8 |
| | 0.4 | B | 80 | 7 | 5 | 8 | 70 | 7 | 5 | 7 |
| | 0.4 | C | 80 | 8 | 5 | 8 | 70 | 7 | 5 | 8 |
| 2/1 | 0.4 | A | 70 | 7 | 5 | 7 | 50 | 7 | 5 | 10 |
| | 0.4 | B | 90 | 7 | 5 | 7 | 70 | 7 | 4.5 | 8 |
| | 0.4 | C | 90 | 7 | 5 | 8 | 70 | 7 | 4.5 | 9 |
| 1/2 | 0.4 | A | 70 | 6 | 5 | 6 | 50 | 7 | 5 | 7 |
| | 0.4 | B | 70 | 7 | 5 | 8 | 50⁺ | 7 | 5 | 8 |
| | 0.4 | C | 70 | 8 | 5 | 7 | 70 | 7 | 5 | 8 |
| 5/1 | 0.4 | A | 80 | 7 | 5 | 11 | 50 | 7 | 4.5 | 13 |
| | 0.4 | B | 90 | 7 | 4.5 | 12 | 70 | 7 | 4.5 | 9 |
| | 0.4 | C | 90 | 7 | 4.5 | 12 | 70 | 7 | 4.5 | 13 |
| 1/5 | 0.4 | A | 70 | 6 | 5 | 6 | 50 | 6 | 5 | 6 |
| | 0.4 | B | 70 | 7 | 5 | 6 | 50 | 7 | 5 | 7 |
| | 0.4 | C | 70 | 7 | 5 | 8 | 50⁺ | 7 | 4.5 | 8 |
| Untreated | 0 | A | 0 | 0 | 5 | 5 | 0 | 0 | 5 | 7 |
| | 0 | B | 0 | 0 | 5 | 7 | 0 | 0 | 5 | 8 |
| | 0 | C | 0 | 0 | 3.5 | 18 | 0 | 0 | 4.5 | 11 |
| 1/1 | 0.2 | C | 80 | 7 | 5 | 10 | 50 | 7 | 5 | 11 |
| Commercially available water and oil-repellant | 0.4 | C | 100 | 6 | 1 | 65 | 80⁺ | 6 | 1 | 63 |
| Commercially available water-repellant | 1.0 | C | 100 | 0 | 1 | 58 | 70⁺ | 0 | 1 | 62 |

In the above table, 50⁻ and 50⁺ represent each below 50 and above 50. The commercially available water and oil-repellant is a composition containing as the main according to Prescription C in Example 22 (total solid fluorocarbon content being 0.6%), the test results on the water-repellency, oil-repellency, stain removability and anti-soil redeposition are shown in the following table:

Table 8

|  | Water repellency | Oil-repellency | Stain removability | Anti-soil redeposition |
|---|---|---|---|---|
| Before laundering | 70 | 7 | 5 | 5–12 |
| After laundering | 50 | 7 | 5 | 8–13 |

EXAMPLE 24

In Emulsion I as described in Example 22, an emulsion of the diester as listed in the following table is incorporated to make a ratio of 1:1 as solid fluorocarbon, and the resultant mixture is subjected to use according to Prescription C so as to make 0.5% concentration of solid fluorocarbon. The fabrics treated with such mixture show the water-repellency (1), oil-repellency (2), stain removability (3) and anti-soil redeposition (4) given in the table.

Table 9

| Diester | Before laundering | | | | After laundering | | | |
|---|---|---|---|---|---|---|---|---|
| | (1) | (2) | (3) | (4) | (1) | (2) | (3) | (4) |
| $R_fOOCCH_2C(=CH_2)$ \| $R_fOOC$ | 80 | 7 | 5 | 9 | 70 | 7 | 5 | 8 |
| $R_fOOC$—⟨benzene⟩—$COOR_f$ | 80 | 6 | 5 | 11 | 50 | 5 | 4.5 | 15 |
| $R^2_fOOCCH_2CH(OH)CH_2COOR^2_f$ | 80 | 7 | 5 | 7 | 50 | 6 | 5 | 8 |
| $R^2_fOOCCH=CHCOOR^2_f$ | 80$^+$ | 7 | 5 | 10 | 70$^-$ | 7 | 5 | 12 |
| $R^3_fOOCCH=CHCOOR^3_f$ | 70 | 7 | 5 | 7 | 50$^-$ | 6 | 5 | 12 |
| $R^3_fOOC(CH_2)_8COOR^3_f$ | 70$^+$ | 6 | 5 | 15 | 50$^-$ | 5 | 4.5 | 18 |
| $R^4_fOOCCH=CHCOOR^4_f$ | 70 | 6 | 5 | 7 | 50$^-$ | 5$^-$ | 4.5 | 11 |

In the above table, Rf represents $(CF_3)_2CF(CF_2CF_2)_n$—$CH_2CH(OH)CH_2$— [n = 3-7; consisting of 56% of the compound (n = 3), 27% of the compound (n = 4), 14% of the compound (n = 5), 2% of the compound (n = 6) and 1% of the compound (n = 7)], $R^2f$ represents $CF_3CF_2(CF_2CF_2)_nCH_2CH(OH)CH_2$— [n = 3-7; consisting of 54% of the compound (n = 3), 28% of the compound (n = 4), 12% of the compound (n = 5), 5% of the compound (n = 6) and 1% of the compound (n = 7)], $R^3f$ represents $(CF_3)_2CF(CF_2)_4CH_2$—$CH(OH)CH_2$— and $R^4f$ represents $CF_3(CF_2)_3CH_2CH(OH)CH_2$—.

EXAMPLE 25

A 10% solution of the polymer obtained by polymerizing $(CF_3)_2CF(CF_2)_4CH_2CH(OH)CH_2OOCC(CH_3)=CH_2$ using azobisisobutyronitrile in a mixture of $CF_2ClCFCl_2$ and acetone (90:10 in weight ratio) and a solution of $(CF_3)_2CF(CF_2CF_2)_nCH_2CH(OH)CH_2$—$OOCCH=CHCOOCH_2CH(OH)CH_2(CF_2CF_2)_nCF(CF_3)_2$ [n = 3-7; consisting of 56% of the compound (n = 3), 27% of the compound (n = 4), 14% of the compound (n = 5), 2% of the compound (n = 6) and 1% of the compound (n = 7)] in a mixture of $CF_2ClCFCl_2$ and acetone (90:10 in weight ratio) are mixed together to make the ratio of each total fluorocarbon content = 1:1. The resulting mixture is diluted with $CF_2ClCFCl_2$ to make a concentration of 0.5 g of total fluorocarbon content per 100 ml. Fabrics made of polyethylene terephthalate fiber and rayon fiber are immersed in the said dilution and dried at room temperature. The water-repellency, oil-repellency, stain removability and anti-soil redeposition of the treated fabrics are as follows:

Table 10

|  | Water repellency | Oil-repellency | Stain removability | Anti-soil redeposition |
|---|---|---|---|---|
| Before laundering | 90 | 7 | 5 | 8 |
| After laundering | 70 | 7 | 5 | 10 |

EXAMPLE 26

Six sheets of a cloth made of polyethylene terephthalate fiber and rayon fiber (80:20) are immersed in a solution of the ester of the formula:

$(CF_3)_2CF(CF_2CF_2)_nCH_2CH(OH)CH_2OOC$—$CH_2$
$(CF_3)_2CF(CF_2CF_2)_nCH_2CH(OH)CH_2OOC$—$COH$
$(CF_3)_2CF(CF_2CF_2)_nCH_2CH(OH)CH_2OOC$—$CH_2$

[n = 9; consisting of 50% of the compound (n = 3), 31% of the compound (n = 4), 12% of the compound (n = 5), 4% of the compound (n = 6) and 3% of the compound (n = 7-9)] (1 g) in a mixture of acetone (10 ml) and trichlorotrifluoroethane (190 ml) and dried at room temperature for about 1 hour. Three sheets of them are subjected as such to the tests for oil-repellency, stain removability and anti-soil redeposition. Other three sheets are laundered with a solution of a cleaning material (37 g) in water (15 L) at 45° C in an automatic washing machine for 10 minutes 5 times, rinsed two times with water for 10 minutes, dried at 80° C for 20 minutes and then subjected to the tests as above. The results are shown in the following table:

Table 11

|  | Oil-repellency | Stain removability | Anti-soil redeposition |
|---|---|---|---|
| Before laundering | 7 | 5 | 9 |
| After laundering | 6 | 4.5 | 8 |

EXAMPLE 27

Fabrics made of polyethylene terephthalate fiber and of polycapramide fiber are immersed in a solution of the ester as used in Example 26 (1 part) in a mixture (100 parts) of acetone and trichlorotrifluoroethane (5:95 in volume ratio), dried in atmosphere and subjected to the tests for oil-repellency, stain removability and anti-soil redeposition. The results are shown in the following table:

Table 12

|  |  | Oil-repellency | Stain removability | Anti-soil redeposition |
|---|---|---|---|---|
| Polyethylene terephthalate fabric | Before laundering | 7 | 4.5 | 8 |
|  | After laundering | 7 | 4.0 | 7 |
| Polycapramide fabric | Before laundering | 7 | 4.5 | 8 |
|  | After laundering | 7 | 4.5 | 7 |

The use of an aqueous dispersion of the said ester (1 g) in a mixture of sodium dodecylbenzenesulfonate (0.25 g), acetone (0.6 g) and water (98.15 g) in place of the above employed treating solution imparts also the same advantageous properties as above to fabrics.

EXAMPLE 28

Cloths made of polyethylene terephthalate fiber and of polycapramide fiber are immersed in a solution of one of the following compounds:

(a) Mellitic acid polyester
[H(CF$_2$)$_6$CH$_2$CH(OH)OOC]$_6$
(b) 1,3,3,5-Pentanetetracarboxylic acid polyester

(c) Trimellitic acid ester

COOCH$_2$CH(OH)CH$_2$(CF$_2$CF$_2$)$_2$CF(CF$_3$)$_2$
— COOCH$_2$CH(OH)CH$_2$(CF$_2$CF$_2$)$_2$CF(CF$_3$)$_2$
COOCH$_2$CH(OH)CH$_2$(CF$_2$CF$_2$)$_2$CF(CF$_3$)$_2$ (d) Alginic acid completely esterified with
CF$_3$(CF$_2$)$_7$CH$_2$CH(OH)CH$_2$OH
(e) Polyacrylic acid ester
COOCH$_2$CH(OH)CH$_2$(CF$_2$)$_6$CF(CF$_3$)$_2$
(—CH$_2$—CH—)$_{300-500}$ (1 g) in a mixture (100 g) of 5% by volume of acetone and 95% by volume of trichlorotrifluoroethane, dried in atmosphere and subjected to the tests for oil-repellency, stain removability and anti-soil redeposition. The results are shown in the following table:

Table 3

|  |  | Oil-repellency | Stain removability | Anti-soil redeposition |
|---|---|---|---|---|
| Mellitic acid polyester | Before laundering | 4 | 3.5 | 15 |
|  | After laundering | 4 | 4 | 16 |
| 1,3,3,5-Pentanetetracarboxylic acid polyester | Before laundering | 4 | 4 | 18 |
|  | After laundering | 3 | 4 | 18 |
| Trimellitic acid ester | Before laundering | 7 | 5 | 8 |
|  | After laundering | 7 | 4.5 | 8 |
| Alginic acid completely esterified | Before laundering | 7 | 4.5 | 15 |
|  | After laundering | 7 | 4.5 | 13 |
| Polyacrylic acid ester | Before laundering | 7 | 5 | 12 |
|  | After laundering | 7 | 4.5 | 12 |

Part B:-

EXAMPLE I

In a 300 ml volume flask equipped with a thermometer, a cooler and a stirrer, $$(CF_3)_2CF(CF_2)_6CH_2\underset{O}{\underset{\diagdown \diagup}{CHCH_2}}$$

(100 g, 0.18 mol) and diethylamine (14.6 g, 0.20 mol) are charged, and the mixture is stirred at 100° C for 3 hours. The resultant viscous liquid is distilled under reduced pressure to give as the fraction (101 g) boiling at 85° to 88° C/0.3 mmHg the tertiary amine of the formula:

$$(CF_3)_2CF(CF_2)_6CH_2CH(OH)CH_2N(C_2H_5)_2$$

Elementary analysis. Calcd.: C, 32.05%; H, 2.67%; F, 60.27%; N, 2.34%. Found: C, 32.60%; H, 2.55%; F, 60.5%; N, 2.4%.

The tertiary amine (1 g) is dissolved in acetone (100 ml), and a broad cloth made of polyethylene terephthalate fiber and cotton fiber is immersed therein and dried. The resultant cloth shows 70 in water-repellency and 6 in oil-repellency.

The above prepared tertiary amine (20 G) and acetic acid (6 g) are put in a 50 ml volume beaker, and the resulting mixture is stirred at 40° C for 10 minutes. By the infrared absorption spectrum and the elementary analysis, the production of the acetate of the said tertiary amine is confirmed.

The acetate is dissolved in water to make 1% aqueous solution. A broad fabric made of polyethylene terephthalate fiber and cotton fiber is immersed in the solution, squeezed to give a pick-up of 100%, dried at 80° C for 10 minutes and then heated at 150° C for 5 minutes. The cloth shows 70 in water-repellency and 6 in oil-repellency.

EXAMPLE II

In a 200 ml volume flask equipped with a thermometer, a stirrer and a cooler,

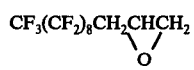

(150 g, 0.28 mol), $CH_3(CH_2)_{17}NH_2$ (38.2 g, 0.14 mol) and triethylamine (2 g) are charged, and the resultant mixture is stirred at 100° to 115° C for 5 hours. After removal of triethylamine under reduced pressure, the resultant pale brown solid (183 g) is recrystallized from benzene to give the tertiary amine of the formula:

Elementary analysis. Calcd.: c, 37.99%; H, 3.69%; f, 54.40%; N, 1.05%. Found: C, 38.2%; H, 3.6%; F, 53.9%; N, 1.1%.

The tertiary amine (1 g) is dissolved in a mixture of trichlorotrifluoroethane (90 ml) and acetone (10 ml). A cloth made of polyethylene terephthalate fiber and cotton fiber is immersed in the solution and dried. The cloth shows 90 in water repellency and 7 in oil-repellency.

EXAMPLE III

In a 1000 ml volume flask equipped with a thermometer, a stirrer and a cooler,

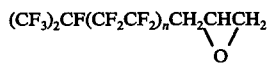

[n = 3-7; consisting of 52% of the compound (n = 3), 25% of the compound (n = 4), 14% of the compound (n = 5), 6% of the compound (n = 6) and 3% of the compound (n = 7)] (300 g, 0.51 mol), pentaethylenehexamine (13.5 g, 0.057 mol) and difluorotetrachloroethane (400 g) are charged, and the mixture is stirred at 95° to 110° C for 8 hours. After removal of difluorotetrachloroethane by distillation under reduced pressure, there is obtained the condensate as pale brown, hard solid (311 g).

EXAMPLE IV

As in Example 10, $H_2NCH_2CH_2CH_2O(CH_2CH_2O)_nCH_2CH_2CH_2NH_2$ (n = 3-140; average molecular weight, 290) (32 g) and $CF_3(CF_2)_6$—

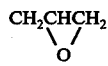

(86 g) are reacted at 90° C for 25 hours. The yellowish brown product is washed with water to give the condensate.

The condensate is treated in a homogenizer as in Example 13 to give an emulsion having a solid concentration of 35%. The emulsion is diluted so as to make 0.75% concentration, and a cloth made of polyethylene terephthalate and rayon (80:20) is immersed and dried. The oil-repellency, stain removability and anti-soil redeposition of the cloth are shown in the following table:

Table I

| | Oil-repellency | Stain removability | Anti-soil redeposition |
| --- | --- | --- | --- |
| Before laundering | 7 | 5 | 11 |
| After laundering | 5 | 4 | 9 |

EXAMPLE V

The condensate (86.5 parts) obtained in Example IV and acetic acid (13.5 parts) are dissolved in water to make a solid concentration of 0.75 g per 100 ml. Fabrics made of polyethylene terephthalate fiber and polycapramide fiber are immersed in the solution, dried and heated at 150° C for 5 minutes. The oil-repellency, stain removability and anti-soil redeposition of the fabrics are shown in the following table:

Table II

| | | Oil-repellency | Stain removability | Anti-soil redeposition |
| --- | --- | --- | --- | --- |
| Polyethylene terephthalate fabric | Before laundering | 7 | 5 | 9 |
| | After laundering | 7 | 4 | 8 |
| Polycapramide fabric | Before laundering | 7 | 4.5 | 9 |
| | After laundering | 6 | 4 | 8 |

EXAMPLE VI

A cloth made of polyethylene terephthalate fiber and cotton fiber is immersed in a solution of $(CF_3)_2CF(CF_2CF_2)_3CH_2$—$CH(OH)CH_2N(C_2H_5)_2$ (1 part) in acetone (100 parts) and dried in atmosphere. Another cloth made of the same fibers as above is immersed in 1% aqueous solution of the acetate of the said amine, dried at 80° C and treated with heat for 5 minutes. These treated cloths are subjected to the tests for water-repellency, oil-repellency, stain removability and recontaminating rate. The results are shown in the following table:

Table III

| Treating agent | Water-repellency | Oil-repellency | Stain removability | Anti-soil redeposition |
| --- | --- | --- | --- | --- |
| Free amine | 0 | 6 | 5 | 8 |
| Acid addition salt | 0 | 6 | 5 | 8 |

EXAMPLE VII

The product (50 g) obtained in Example III is added to glacial acetic acid (10 g), and the resultant mixture is agitated while heating at 80° C whereby the acetate soluble in water is yielded. In a 1% solution of the acetate in water, there is immersed a cloth made of polyethylene terephthalate fiber or of polycapramide fiber, and the cloth is squeezed to remain about 80% by weight of the solution to the amount of the cloth, dried at 80° C for 20 minutes and then heated at 150° C for 5 minutes. The cloth is separated into two portions, of which one is subjected as such to the tests for water-repellency, oil-repellency, stain removability and anti-soil redeposition. The other portion is washed 5 times with a solution of a cleaning material (37 g) in water (15 L) at 45° C in an automatic washing machine for 10 minutes, rinsed two times with water for 10 minutes, dried at 80° C for 20 minutes and then subjected to the tests as above. The results are shown in the following table:

Table IV

| | | Water-re-pellency | Oil-re-pellency | Stain remov-ability | Anti-soil redeposition |
|---|---|---|---|---|---|
| Poly-ethylene tereph-thalate fabric | Before laundering | 80 | 7 | 5.0 | 8 |
| | After laundering | 70 | 7 | 5.0 | 7 |
| Poly-capr-amide fabric | Before laundering | 80 | 7 | 5.0 | 8 |
| | After laundering | 80 | 7 | 5.0 | 7 |

The use of an aqueous dispersion of the free amine (15 g) produced in Example III in a mixture of dimethyloc-tadecylamine acetate (2g), acetone (5 g) and water (78 g) in place of the above employed treating solution imparts also the same advantageous properties as above to fabrics.

The results of the tests carried out using known treating agents for fabrics made of polyethylene terephthalate fiber are shown in the following table:

Table V

| | | Water-re-pellency | Oil-re-pellency | Stain remova-bility | Anti-soil redeposition |
|---|---|---|---|---|---|
| Polymer of per-fluoro-alkane-sulfonyl-acryl-amide | Before laund-dering | 90 | 7 | 2 | 50 |
| | After laun-dering | 80 | 7 | 2 | 67 |
| Copolymer of ethyl-acrylate and acrylic acid | Before laun-dering | 0 | 0 | 5 | 11 |
| | After laun-dering | 0 | 0 | 3 | 12 |

What is claimed is:
1. A compound of the formula:

[RfCH$_2$CH(OH)CH$_2$OOC]$_2$Q wherein Rf is a perfluoroalkyl group, an ω-hydro-perfluoroalkyl group or an ω-chloro-perfluoroalkyl group having 4 to 20 carbon atoms and Q is —AO(CH$_2$CH$_2$O)$_q$A— wherein A is —R$^1$—, —COCH=CH—, —COCH=CHCOO(CH$_2$CH$_2$O)$_r$COCH=CH— or

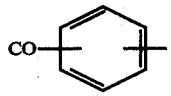

in which R$^1$ is a lower alkylene group having 1 to 3 carbon atoms and $q$ and $r$ are each 4 to 140.